United States Patent [19]

Wagner et al.

[11] 4,166,104

[45] Aug. 28, 1979

[54] SPECIFIC BINDING ASSAY METHOD AND TEST KIT EMPLOYING POLYSTYRENE AS SEPARATING AGENT

[75] Inventors: Daniel B. Wagner; Zvi Gross, both of Jerusalem, Israel

[73] Assignee: Ames-Yissum Ltd., Jerusalem, Israel

[21] Appl. No.: 852,104

[22] Filed: Nov. 16, 1977

[30] Foreign Application Priority Data

Nov. 19, 1976 [IL] Israel ............................................ 50944
Jan. 6, 1977 [IL] Israel ............................................ 51224

[51] Int. Cl.² ...................... G01N 33/16; A61K 23/00; B65D 81/32
[52] U.S. Cl. ...................................... 424/1; 23/230 B; 206/569; 424/12
[58] Field of Search ................... 424/1, 12; 73/230 B, 73/259; 206/569

[56] References Cited

U.S. PATENT DOCUMENTS

| | | | |
|---|---|---|---|
| 4,001,583 | 1/1977 | Barrett | 424/1 |
| 4,020,151 | 4/1977 | Bolz et al. | 424/1.5 |
| 4,048,298 | 9/1977 | Niswender | 424/1.5 |
| 4,069,352 | 1/1978 | Parsons, Jr. | 424/1 |

OTHER PUBLICATIONS

Ed. Croll et al., New Techniques In Tumor Location and Radioimmunoassay, J. Wiley & Sons, NY, 1975, pp. 9–15.

*Primary Examiner*—Benjamin R. Padgett
*Assistant Examiner*—Christine M. Nucker
*Attorney, Agent, or Firm*—Andrew L. Klawitter

[57] ABSTRACT

A specific binding assay method and test kit for determining a ligand, particularly an antigen or hapten, in, or the ligand binding capacity of, a liquid medium, particularly a body fluid such as serum, wherein the liquid medium is combined with assay reagent means including a labeled binding component, such as a radiolabeled form of the ligand, with the improvement that separation of the resulting bound-species and free-species of the labeled component is accomplished by selectively adsorbing the free-species onto a solid comprising a nonion-exchange cross-linked styrene polymer. The method is particularly suited to the radioimmunoassay detection of nonproteinaceous haptens such as thyroxine, triiodothyronine, estriol, vitamin $B_{12}$ and digoxin. The styrene polymer adsorbent provides a very effective and readily available separation means for use in specific binding assays.

34 Claims, 3 Drawing Figures

FIG. I

SPECIFIC BINDING ASSAY METHOD AND TEST KIT EMPLOYING POLYSTYRENE AS SEPARATING AGENT

BACKGROUND OF THE INVENTION

1. Field of the Invention

This invention relates to the quantitative determination of substances in or characteristics of liquid media, including body fluids such as serum, based on specific binding assay techniques. In particular, the invention is directed to the detection of antigens or haptens based on immunoassay techniques involving the use of labeled reagents, such as radiolabeled reagents. The present invention provides an improved method of performing the separation of bound- and free-label inherent in heterogeneous specific binding assays.

2. Description of the Prior Art

A living system is able to detect, recognize and respond to the presence of foreign material (antigen) such as protein, virus, bacteria, and so forth, within that system. This response takes, inter alia, the form of producing an antibody specific for the particular antigen. There then occurs a specific reaction between the antibody and the antigen to form a complex. An antibody once produced is also capable of binding a hapten, i.e., a relatively small and simple compound which may be the determinant group of a given antigen, which hapten is capable of binding with the specific antibody but incapable itself of giving rise to the production of an antibody, unless it is bound to an antigenic carrier.

The binding interaction between an antigen or a hapten and its antibody is specific and sensitive. Other types of materials that participate in similar specific and sensitive binding interactions are enzymes and their substrates; materials such as hormones, vitamins, metabolites and pharmacological agents, and their receptors and binding substances; and other substances known in the science. These specific and sensitive binding reactions have given rise to a rapidly emerging analytical technique known as the specific binding assay technique. In one such type of assay method, the substance, or group of substances, to be determined (herein referred to as "ligand") in a liquid sample is placed in competition with a labeled form of the ligand or of a binding analog thereof for binding to a binding reagent. Where a radioactive label is used and the binding reagent is an antibody, the method is known as a radioimmunoassay method. Recently, several alternative labeling materials have been reported for replacement of radioisotopes, including enzymes, co-enzymes, enzyme substrates, enzyme modulators such as inhibitors and allosteric effectors, fluorescent molecules, luminescent molecules, and others. For illustrative purposes, the discussion which follows describes one particular type of specific binding assay technique, a competitive binding radioimmunoassay technique.

This system consists of antigen or hapten labeled with a radioactive marker, unlabeled native antigen (in the test sample) and specific antibody whereby there is competition between the unlabeled antigen and the labeled antigen for binding to a limited amount of antibody. Hence, the greater the concentration of unlabeled antigen from the test sample in the system, the less the labeled antigen will be bound by the antibody. This may be diagrammatically represented as follows:

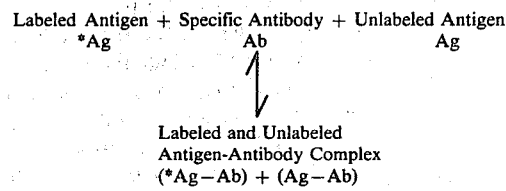

Labeled Antigen + Specific Antibody + Unlabeled Antigen
 *Ag                    Ab                         Ag Labeled and Unlabeled
Antigen-Antibody Complex
(*Ag—Ab) + (Ag—Ab)

If the concentration of labeled antigen and antibody is fixed and the only variable is the level of unlabeled antigen, it becomes possible to establish an assay system for measuring the unknown level of unlabeled antigen by physically separating the antigen-antibody complex from the remaining free antigen (both labeled and unlabeled). The radioactivity of the unknowns is compared with a standard curve plotting of the values given by a range of known amounts of the antigen treated in the same manner.

There are many known procedures for separating the free unbound antigen or hapten from the complex antigenantibody. One method known as chromatoelectrophoresis combines techniques of paper chromatography and paper electrophoresis. Paper with a high affinity for the free antigen (such as Whatman 3 MM, Whatman 3MC and DEAE paper) are used as carriers. While this technique is discriminative and has been used in the assay of insulin, growth hormone, glucagon, parathyroid hormone, thyroid stimulating hormone and other peptide hormones, it has a number of prominent disadvantages which limits its use. A limited amount of material may be applied to the absorbent, and the separation is both laborious and time-consuming.

By another known method the antigen-antibody complex is precipitated by salts, organic material or solvents under conditions that do not affect the free antigen. Among the salts, materials and solvents used are: ethanol, acetone, sodium sulfate, ammonium sulfate, dioxane, tricholoacetic acid, polyethylene glycol, and so forth. The use of salts, solvents or organic materials has the advantage that the separation is immediate, and a second incubation is not necessary. However, the chemical precipitation technique may cause the co-precipitation of other proteins, often causing an incomplete separation of the two fractions.

There is also known the double antibody technique, which is widely used for the separation of the bound and the free antigen. By this method a second antibody that was raised against the first antibody is used to precipitate the primary antigen-antibody complex. For example, if the first antibody was raised in a rabbit then the second antibody may be an antiserum to rabbit gammaglobulin raised in goats. One disadvantage of this technique is that the use of a second antibody introduces an additional incubation. Specific binding assay methods employing a double antibody separation technique are described in U.S. Pat. Nos. 3,839,153 and 3,872,225.

Furthermore, there are known various solid-phase techniques for the separation of free and bound antigen. These techniques make use of antibodies covalently bound or physically adsorbed to an insoluble matrix (immunosorbents), such as bentonite, cellulose, bromacetyl cellulose, the cross-linked dextrans (Sephadex), sepharose, plastic (non-cross-linked polystyrene or polypropylene) beads, Enzacryl AA, nitro-cellulose membranes, and so forth. The formed antibody-antigen complex is held by the solid phase and the bound fraction can be separated from the free fraction by filtration.

By yet another method the free (unbound) antigens are bound to adsorbents which then can be precipitated by centrifugation. Powdered talc (magnesium silicate), Kaolin (aluminum silicate), QUSO (microgranules of silica), cellulose powder, and so forth, are some of the simple adsorbents used. Many separations are performed by using adsorbent charcoal coated with dextran. The dextran behaves rather like a sieve which allows the smaller molecules of free antigen to pass and these are then bound by the charcoal, leaving the bound antigen in solution, after the charcoal has been removed by centrifugation or filtration.

The prior art also describes the use of specific cross-linked polystyrene materials to extract steroids from solutions, Steroids 11(3):265-272(1968), Fed. Proc. 26(2):425(1967), Acta Endocrinol. (Suppl) 147:144-154(1970), Principles of Competitive Protein-Binding Assays, ed. Odell and Daughaday, Chap. XI, pp. 303-323(1972), Steroids 15(1):73-88(1970), and Steroids 22(6):795-811(1973). These techniques have not been applied to specific binding assays wherein the polystyrene materials serve as adsorbent directly in the binding assay reaction and, in fact, subsequent teachings have been away from such use, Clin. Chim. Acta 63:303-308(1975) and Clin. Chem. 19(9):1016-1021(1973).

It is also known to use ion exchange and other types of resins to bind free antigens by electrostatic forces and this method has been used so far mainly for the determination of small molecules such as thyroid hormones (T-3 and T-4). Examples of this type of methodology are described in U.S. Pat. Nos. 3,659,104; 3,710,117 and 3,961,894.

One technique of this type used for the separation of the antigen-antibody complex from free antigen employs a column packed with material which preferentially adsorbs either the free antigen or the antigen-antibody complex. The incubated aqueous reaction mixture is applied to the head of such a column and the column is then eluted. The radioactivity of either the column or the eluate is then determined and the content of the antigen in the starting solution is calculated from the count.

SUMMARY OF THE INVENTION

Accordingly the present invention provides, in a specific binding assay method for determining a ligand in or the ligand binding capacity of a liquid medium, wherein said liquid medium is combined with assay reagent means including a binding component incorporated with a label to form a binding reaction system having a bound-species and a free-species of said labeled component, wherein said bound-species and said free-species of said labeled component are separated, and wherein said label is measured in one of said separated bound-species and free-species of the labeled component, the improvement which comprises accomplishing said separation by selectively adsorbing said free-species of the labeled component onto a solid comprising a nonion-exchange cross-linked styrene polymer.

The novel adsorbent finds major application to the detection of a nonproteinaceous hapten such as thyroxine, triiodothyronine, estriol, vitamin $B_{12}$, and digoxin.

DESCRIPTION OF THE PREFERRED EMBODIMENTS

Figure 1:
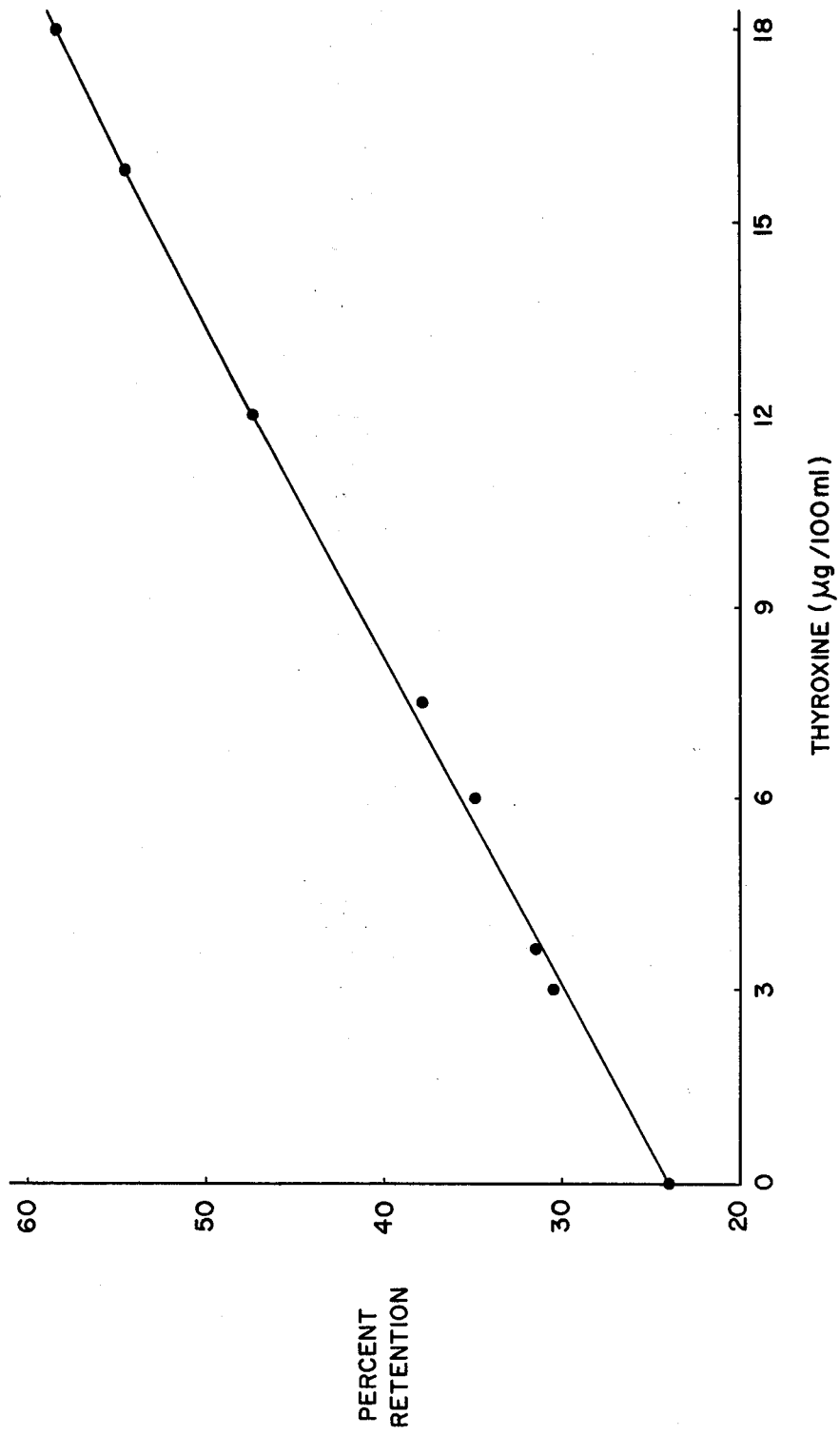
FIG. 1 is an illustrative standard curve used in the determination of thyroxine following a competitive binding radioimmunoassay technique.

In the context of this disclosure, the following terms shall be defined as follows: "ligand" is the substance, or group of substances, whose presence or the amount thereof in a liquid medium is to be determined; "binding agent for the ligand" is any substance, or group of substances, which has a specific binding affinity for the ligand to the exclusion of other substances; and "binding analog of the ligand" is any substance, or group of substances, which behaves essentially the same as the ligand with respect to the binding affinity of the binding agent for the ligand.

The use of the novel adsorbent as separating means may be applied to any of the various types of heterogeneous specific binding assay formats such as the competitive binding technique discussed above or the sequential saturation technique wherein sample ligand is exposed to an excess amount of binding agent and the resulting unsaturated sites in the binding agent are bound by labeled ligand or analog by exposure to an excess amount of the labeled component. The amount of remaining free-labeled component is separated and is directly related to the amount of unknown ligand in the sample.

Upon completion of the binding reaction, the reaction mixture is exposed to the novel adsorbent allowing the free-species of the labeled component to become selectively adsorbed thereto, and the adsorbent carrying the adsorbed species is physically separated from the reaction mixture. Thereafter, the label is measured in the remaining reaction mixture or on the adsorbent. The exposure of the adsorbent to the reaction mixture and subsequent separation thereof can be accomplished in many different ways.

In one aspect, the adsorbent may be in a particulate form such as in the form of powder, beads, pellets, granules, crystals, filaments, and so forth. The particulate adsorbent may be simply added as such to the reaction mixture and separation accomplished by centrifugation, filtration, and the like. Alternatively, the particulate adsorbent may be contained in a column and exposure to and separation from the reaction mixture can be carried out by passing same through the column. Such passage may comprise allowing the reaction mixture to percolate and/or be washed by downward gravitational flow of the reaction mixture through the column or by drawing the reaction mixture into the column such as in the manner described in an application filed on even data herewith entitled "Column Chromatography Specific Binding Assay Method and Test Kit", Ser. No. 852,105, based on Israel patent application No. 51,354, assigned to the instant assignee.

In another aspect, the adsorbent may take the form of a solid composite body such as a solid carrier inert to the reaction mixture impregnated or coated with the adsorbent. In use, the adsorbent-carrier device is immersed in the reaction mixture and after a set period of time simply removed therefrom to effect the necessary separation. This embodiment is particularly attractive in practicing the present method, since it can be carried out in any ordinary laboratory vessel, such as a test tube. For this particular embodiment the composite adsorbent body may be fitted with a handle which may be permanently or detachably connected thereto. The composite body may be of any desirable shape. If it is intended to be used inside columns it is preferably in the form of a disc or cylinder. In practicing this particular embodiment the number of individual bodies packed into one column will depend on the adsorption capacity of the composite body and the concentration of ligand in the reaction mixture. The composite body can be prepared by conventional impregnation and coating techniques. Preferably, the carrier will first be impregnated or coated with the adsorbent such as by immersion in a bath of a suitable solution, followed by contacting the thus impregnated or coated carrier with a solution containing a cross-linked agent, again best by immersion.

In accordance with one preferred embodiment of the present invention previously discussed, separation is accomplished using adsorption columns packed with a particulate form of the adsorbent. For the preparation of such columns it is, for example, possible to use plastic syringe barrels. Each barrel is prefitted with a bottom closure means, for example, a removable cap, and a detergent treated sintered porous ethylene polymer (homopolymer or copolymer thereof) retaining disc is pressed coaxially to the bottom of the plastic barrel. After placement of the granular adsorbent in the syringe barrel it is, if necessary, washed with a buffer and is then permitted to settle free of air bubbles after which another porous, detergent treated sintered ethylene polymer (homopolymer or copolymer thereof) disc, similar to the first mentioned disc, is inserted into the syringe barrel and pushed coaxially into firm contact with the granular adsorbent. The amount of the granular adsorbent inside the columns depends on the type of adsorbent and the type of the test for which the column is prepared. The column thus prepared is then washed with an appropriate buffer. For performing a measurement in accordance with this embodiment, the reaction mixture is prepared and incubated in the top region of the column. The column is then unsealed from below so that the aqueous phase can flow through and the column is then washed with buffer to wash away any residual amounts of the unabsorbed bound-species.

In preferred embodiment, the detection of a nonproteinaceous hapten in the liquid medium, usually aqueous, is carried out by an improved radioimmunoassay method of the type wherein said aqueous medium is mixed with a radiolabeled form of said hapten or of a binding analog thereof and with an antibody for said hapten and the resulting reaction mixture is incubated to form a bound-species of said radiolabeled hapten or analog wherein such is bound to said antibody and a free-species of said radiolabeled hapten or analog wherein such is not bound to said antibody, wherein said bound-species and said free-species are separated, and wherein the radioactivity of one of said separated bound-species and said free-species is measured. The improvement of the present invention comprises accomplishing said separation of said bound-species and said free-species by contacting said reaction mixture with the novel adsorbent described herein.

From the total radioactivity ("initial" count) and the radioactivity of the separated adsorbent upon conclusion of the assay ("final" count), the percent retention is calculated by the following formula:

$$\text{percent retention} = \frac{\text{final count}}{\text{initial count}} \times 100$$

For the determination of unknown quantities of the hapten, it is first necessary to perform a series of assays with varying known amounts of hapten, thereby to establish a standard percent retention versus concentration curve. This curve is then used to determine an unknown concentration from the percent retention calculated from radioactivity counts.

In principle, the total radioactivity is determined by the amount of radioactively labeled hapten or analog used for the preparation of the reaction mixture. However, to avoid inaccuracies due to imprecise application of the labeled component, it may be preferable to establish the total radioactivity experimentally. This may be done either before or after the selective determination of the radioactivity of the separated adsorbent. The total radioactivity may be determined after incubation and before actual separation of the adsorbent column and the remaining reaction mixture.

The present invention also provides a method for determining the ligand binding capacity of a liquid medium. In such an assay, the liquid medium is suspected of containing a binding agent for the ligand. For example, the method according to the invention can be modified for the performance of the so called "T-3 Uptake Test". In this test, the thyroid hormone in serum is indirectly assayed by determining the available binding sites on thyroid binding globulin (TBG) present in the serum. In this test, it is assumed that the amount of TBG in normal sera is relatively constant and that it binds most of the available thyroid hormone. When labeled T-3 (triiodothyronine) is added to a serum sample, it will be bound by the TBG in proportion to the residual binding sites available thereon. Thus, if it is found that a large amount of labeled T-3 is bound by the serum, this indicates a large number of available binding sites and hence a low level of thyroid hormone, and vice versa. Measurement of the unbound labeled T-3 can thus be related to thyroid function. In the clinical application of the T-3 uptake test, it suffices in many cases to determine the T-3 uptake ratio in comparison with a standard normal serum. This ratio can be derived by dividing the initial count (as defined above) obtained from the unknown sample by the initial count of a standard serum sample which has been subjected to a parallel, identical assay procedure.

In preferred embodiment, the determination of the binding capacity of a liquid medium, usually aqueous, for a non-proteinaceous hapten, is carried out by an improved radioassay method of the type wherein said aqueous medium is mixed with a radiolabeled form of said hapten or of a binding analog thereof and the resulting mixture is incubated to form a bound-species of said radiolabeled hapten or analog wherein such is bound to a binding agent of said aqueous medium and a free-species of said radiolabeled hapten or analog wherein such is not bound to said binding agent, wherein said bound-species and said free-species are separated, and wherein the radioactivity of one of said separated bound-species and said free-species is measured. The improvement of the present invention comprises accomplishing said separation of said bound-species and said free-species by contacting said reaction mixture with the novel adsorbent described herein.

The present invention also provides a test kit for carrying out the present method. A test kit is provided for determining a ligand in a liquid medium, comprising (1) said ligand, or a binding analog thereof, incorporated with a label, such as a radioactive atom, (2) a binding agent for said ligand, such as an antibody, and (3) a solid nonion exchange cross-linked styrene polymer. Also provided is a test kit for determining the ligand binding capacity of a liquid medium, comprising (1) said ligand, or a binding analog thereof, incorporated with a label, such as a radioactive atom, and (2) a solid nonion exchange cross-linked styrene polymer. Such test kits preferably comprise said styrene polymer in a particulate form and contained in a column, or incorporated with a carrier matrix, as described in detail hereinbefore.

The present invention will now be illustrated, but is not intended to be limited, by the following examples.

PREPARATION OF COLUMNS

The columns were prepared by packing 1.0 gram of styrene polymer beads (Amberlite XAD-2 type, obtained from BDH Chemicals, Poole, a nonion-exchange, cross-linked styrene polymer which is a styrene-divinylbenzene copolymer U.K.) into 5 ml plastic syringe barrels prefitted with a removable bottom cap and a detergent-treated sintered, porous retaining disc cut from a sheet of copolymer of ethylene and vinylacetate (EVA) (Porvair Ltd., King's Lynn, Norfolk, England). Two (2) ml of barbital buffer (2.33 gr sodium barbital and 0.724 gr ethylenedinitrilotetraacetate in 150 ml water, pH 8.6) were added, followed by a second detergent-treated, sintered, porous disc as described above, which was pressed parallel to the first one with a plunger. The bottom cap was removed and the styrene polymer columns were washed with 3 ml of barbital buffer, after which the cap was replaced.

EXAMPLE 1

Radioimmunoassay for Thyroxine (T-4)

In order to perform a radioimmunoassay for T-4, the following reagents were added to the barbital buffer washed styrene polymer columns (all reagents were dissolved in barbital buffer):

1. 100 µl ANS solution (8-anilino-1-naphthalene sulfonic acid, ammonium salt, 4.0 g/liter).
2. 100 µl $^{125}$I-T-4 (about 40,000 cpm).
3. 100 µl T-4 standard (in concentration range of 6-36 µg/liter) or a 1:5 diluted clinical serum sample.
4. 100 µl anti-T-4 antibody.

The columns were gently shaken in order to assure thorough mixing of the reagents, and after five minutes of incubation at room temperature, the bottom cap was removed and the reaction mixture was allowed to penetrate into the styrene polymer beads. The amount of radioactivity in each column was determined ("initial count"). Each column was then washed with 3.0 ml of buffer and a second reading of the radioactivity of the columns was taken ("final count"). The "percent retention" of each column was calculated using the equation:

$$\text{percent retention} = \frac{\text{final count}}{\text{initial count}} \times 100$$

A standard curve was obtained by plotting the percent retention values versus the corresponding concentration of thyroxine, the T-4 standard (FIG. 1).

Results obtained with known reference sera and clinical sera samples:

| Known Concentrations of T-4 in Reference Sera (µg/100 ml) | | Concentrations of T-4 Found Using the Assay Described in this Example (µg/100 ml) | | |
|---|---|---|---|---|
| Lederle II | 16–24 (a) | 16.5; 17; 21; 18.7 | | |
| NMS II | 16–19 (b) | 16.5; 18; 21; 21.5 | | |
| Clinical Samples with Assigned Values of T-4 | | | | |
| 2.2 | | 2.2 | | |
| 3.3 | | 3.8; | 2.8 | |
| 4.5 | | 4.5 | | |
| 7.2 | | 7.4; | 7.4; | 6.5 |
| 15 | | 18; | 15.4 | |
| 17.7 | | 17.9 | | |
| 18 | | 17.8 | | |
| 20 | | 20; | 21; | 21.8 |

(a) Supplied by Lederle Diagnostics, American Cyanamid Company, Pearl River, N.Y., U.S.A.
(b) Supplied by Nuclear Medical Systems Inc., 515 Superior, Newport Beach, CA., U.S.A.

Unknown amounts of T-4, e.g., in serum, can be determined in the above manner with aid of the standard curve of FIG. 1.

EXAMPLE 2

Radioimmunoassay for Digoxin

The buffer used in this test was a phosphate buffer, pH 7.4 (6.25 g. sodium biphosphate/liter; the pH is adjusted with NaOH solution).

Styrene polymer columns were prepared as described above, and washed with 3.0 ml phosphate buffer. The following solutions were added on top of the columns in the indicated order:

1. 200 µl $^{125}$I-digoxin (27,000 cpm).
2. Standard digoxin. The standards were prepared by diluting 1 ml of stock solutions having concentrations of 0.5, 1.0, 2.0 and 5.0 ng/ml with one ml normal serum, and one ml buffer. From these diluted (1:3) standards, 200 µl were added to the colums.
3. 200 µl antiserum (antidigoxin rabbit antiserum diluted 1:40,000 in phosphate buffer containing 0.2% bovine serum albumin, BSA).

The reaction mixture was incubated for 40 minutes at room temperature, allowed to penetrate into the columns, and the first reading of the radioactivity was taken. The columns were washed with 3.0 ml phosphate buffer, and the second reading was taken. The percent retention was calculated as above, and a standard curve (FIG. 2) was obtained in a similar manner.

Figure 2:
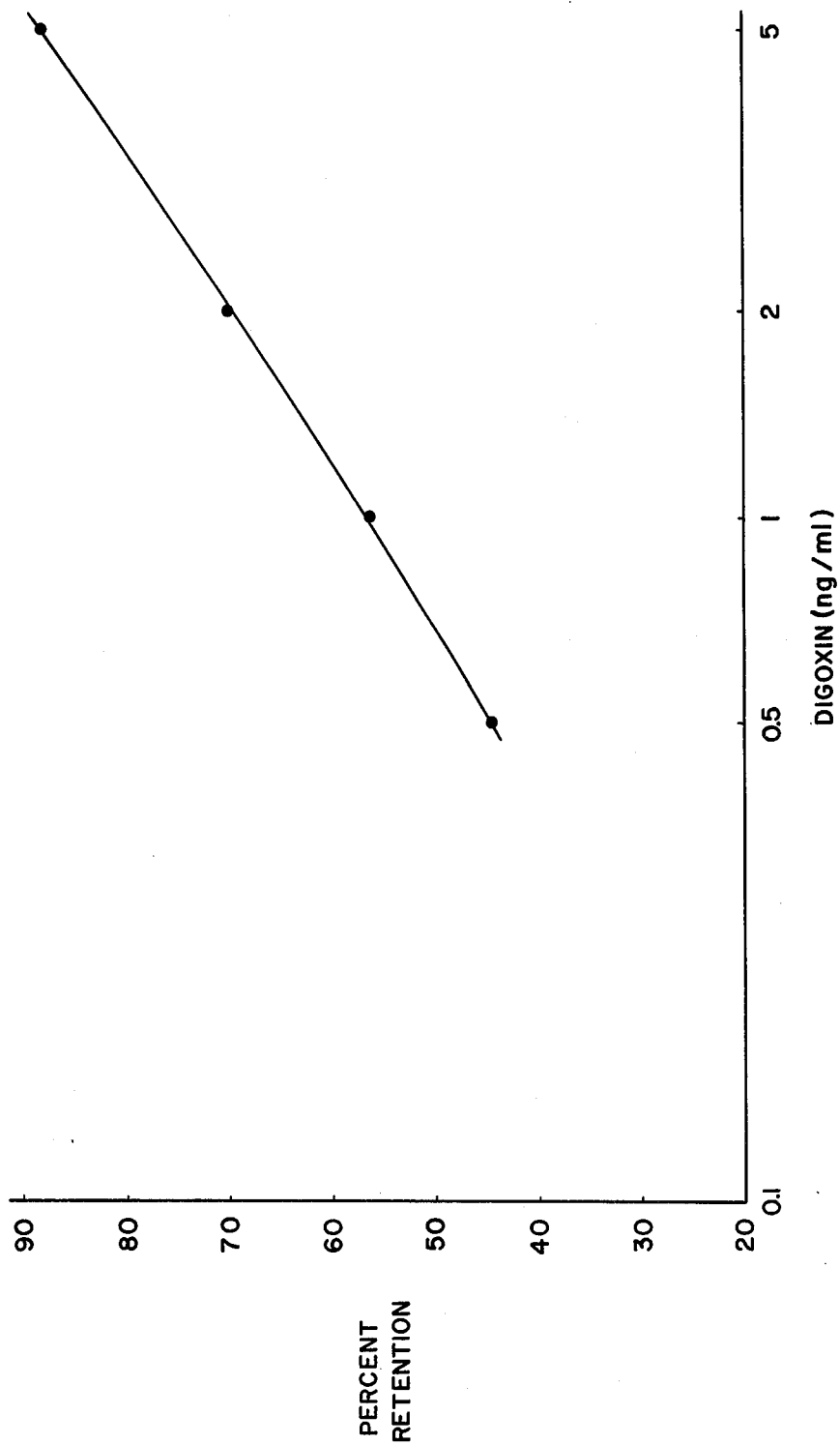
FIG. 2 is an illustrative standard curve for use in the determination of digoxin following a competitive binding radioimmunoassay technique.

Unknown amounts of digoxin, e.g., in serum, can be determined in the above manner with the aid of the standard curve of FIG. 2.

Results obtained with clinical sera samples:

| Clinical Sera Samples with Assigned Values of Digoxin (ng/ml) | Concentrations of Digoxin Found Using the Assay Described in this Example (ng/ml) |
|---|---|
| 0.62 | 0.61 |
| 0.82 | 0.8 |
| 1.1 | 0.98 |
| 1.21 | 1.3 |
| 1.26 | 1.34 |
| 1.65 | 1.97 |
| 1.92 | 1.79 |
| 3.32 | 3.66 |

EXAMPLE 3

Radioimmunoassay for Vitamin $B_{12}$

The buffer used in this test was a 0.1 M borate-carbonate, pH 8.8 (prepared by dissolving 1.1 g disodium carbonate and 1.55 g boric acid in 250 ml of distilled water). The polystyrene columns were prepared as described above, and washed with 5.0 ml of borate-carbonate buffer. The test was performed by applying the following solutions on top of the columns:

1. 0.5 ml vitamin $B_{12}$ standard (in concentrations of 0.0, 50, 200 and 2000 pg/ml) or the tested sample to be assayed.
2. 0.2 ml $^{57}$Co-vitamin $B_{12}$ (about 4000 cpm).
3. 0.2 ml chicken serum.

The reaction mixture was allowed to incubate for one hour, after which it was allowed to penetrate into the columns. After the radioactivity of the columns was measured, 5.0 ml of borate-carbonate buffer was allowed to flow through each column and a second reading of the radioactivity was taken. The calibration curve (FIG. 3) was constructured as described in the Examples above.

Figure 3:
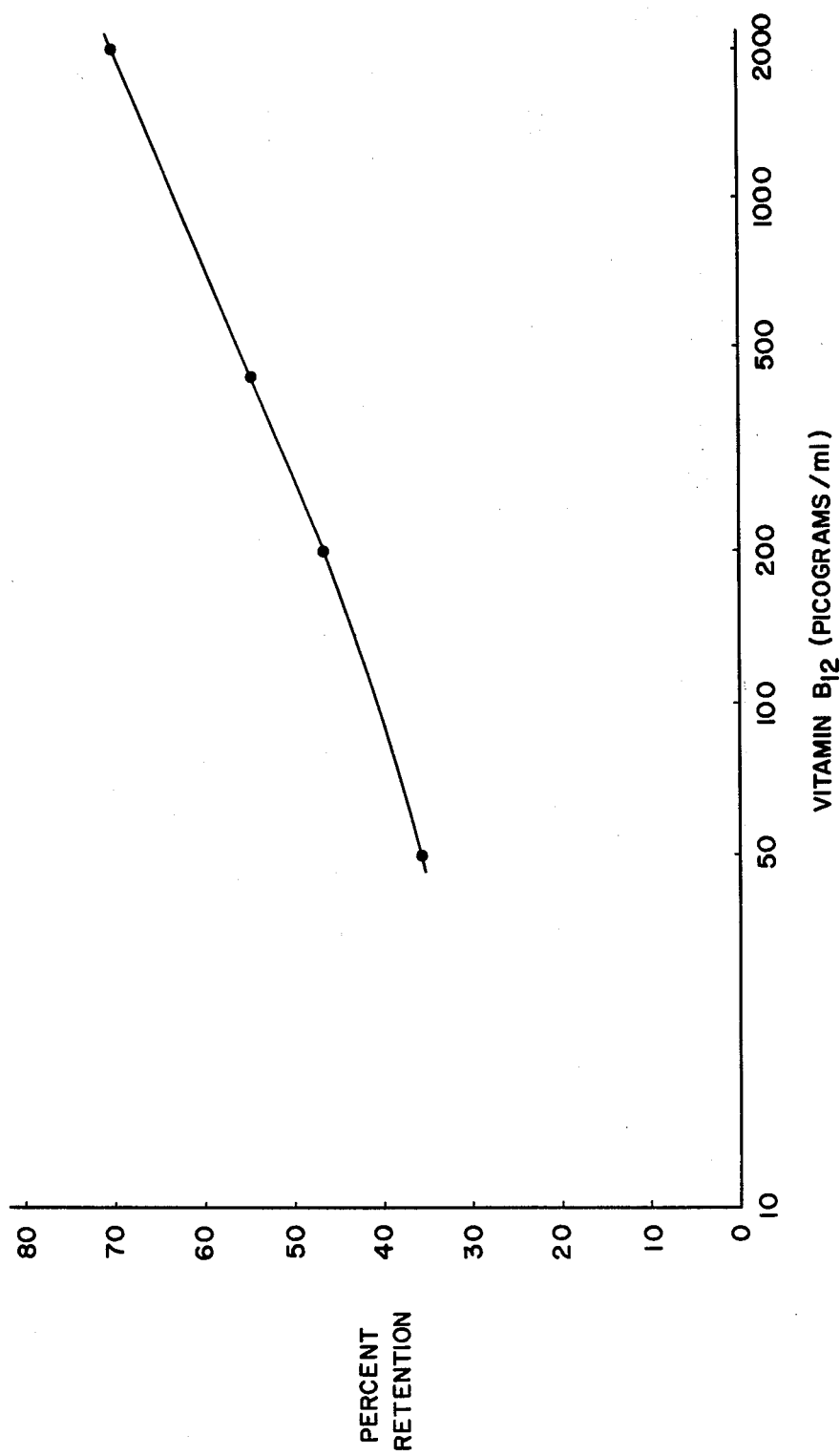
FIG. 3 is an illustrative standard curve for use in the determination of vitamin $B_{12}$ following a competitive binding radioimmunoassay technique.

Unknown amounts of vitamin $B_{12}$, e.g., in serum, can be determined in the above manner with the aid of the standard curve of FIG. 3.

What is claimed is:

1. In a specific binding assay method for determining a ligand in or the ligand binding capacity of a liquid medium,
   wherein said liquid medium is combined with assay reagent means including a binding component incorporated with a label to form a binding reaction system having a bound-species and a free-species of said labeled component,
   wherein said bound-species and said free-species of said labeled component are separated, and
   wherein said label is measured in one of said separated bound-species and free-species of the labeled component,
   the improvement which comprises accomplishing said separation by selectively adsorbing said free-species of the labeled component onto a solid comprising a nonion-exchange cross-linked styrene polymer, said styrene polymer being a styrene-divinylbenzene copolymer.

2. The method of claim 1 wherein said ligand is a nonproteinaceous hapten.

3. The method of claim 2 for determining said hapten in an aqueous liquid wherein said assay reagent means includes (i) as labeled component, said hapten or a binding alalog thereof incorporated with a label and (ii) a specific binding agent for said hapten.

4. The method of claim 3 wherein said hapten is thyroxine.

5. The method of claim 3 wherein said hapten is triiodothyronine.

6. The method of claim 3 wherein said hapten is estriol.

7. The method of claim 3 wherein said hapten is vitamin $B_{12}$.

8. The method of claim 3 wherein said hapten is digoxin.

9. The method of claim 3 wherein said specific binding agent is an antibody for said hapten.

10. The method of claim 3 wherein said label is a radioactive atom.

11. The method of claim 2 for determining the binding capacity of an aqueous liquid for said hapten wherein said assay reagent means includes, as labeled component, said hapten or a binding analog thereof incorporated with a label.

12. The method of claim 11 wherein said hapten is triiodothyronine.

13. The method of claim 11 wherein said label is a radioactive atom.

14. The method of claim 1 wherein said assay reagent means includes a specific binding agent for said labeled component.

15. The method of claim 14 wherein said binding agent is an antibody for said ligand.

16. The method of claim 1 wherein said styrene polymer is in a particulate form.

17. The method of claim 16 wherein said separation is accomplished by adding said particulate form of said styrene polymer to said reaction mixture and thereafter separating such by centrifugation or filtration.

18. The method of claim 16 wherein said particulate form of said styrene polymer is contained in a column and wherein said separation is accomplished by passing said reaction mixture through said column.

19. The method of claim 1 wherein said styrene polymer is incorporated with a carrier matrix and wherein said separation is accomplished by contacting said carrier matrix with said reaction mixture and thereafter removing same therefrom.

20. A test kit for determining a ligand in a liquid medium, comprising, in package combination,
   (1) a container of said ligand or a binding analog thereof incorporated with a label,
   (2) a container of a binding agent for said ligand, and
   (3) a solid adsorbent comprising a nonion-exchange crosslinked styrene polymer, said styrene polymer being a styrenedivinylbenzene copolymer.

21. The test kit of claim 20 wherein said ligand is a nonproteinaceous hapten.

22. The test kit of claim 20 wherein said hapten is thyroxine, triiodothyronine, estriol, vitamin $B_{12}$ or digoxin.

23. The test kit of claim 20 wherein said specific binding agent is an antibody.

24. The test kit of claim 20 wherein said label is a radioactive atom.

25. The test kit of claim 20 wherein said styrene polymer is in a particulate form.

26. The test kit of claim 25 wherein said particulate form of said styrene polymer is contained in a column.

27. The test kit of claim 20 wherein said styrene polymer is incorporated with a carrier matrix.

28. A test kit for determining the ligand binding capacity of a liquid medium, comprising, in package combination,
(1) a container of said ligand or a binding analog thereof incorporated with a label, and
(2) a solid adsorbent comprising a nonion-exchange crosslinked styrene polymer, said styrene polymer being a styrenedivinylbenzene copolymer.

29. The test kit of claim 28 wherein said ligand is a nonproteinaceous hapten.

30. The test kit of claim 28 wherein said ligand binding capacity is the capacity for binding for triiodothyronine.

31. The test kit of claim 28 wherein said label is a radioactive atom.

32. The test kit of claim 28 wherein said styrene polymer is in a particulate form.

33. The test kit of claim 32 wherein said particulate form of said styrene polymer is contained in a column.

34. The test kit of claim 28 wherein said styrene polymer is incorporated with a carrier matrix.

* * * * *